(12) United States Patent
Leonard

(10) Patent No.: US 10,383,899 B2
(45) Date of Patent: Aug. 20, 2019

(54) IMMUNITY GENERATION

(71) Applicant: IMMUNE MACRO-BIOTIC TECHNOLOGY UK LIMITED, Torquay (GB)

(72) Inventor: Christopher Jeremy Leonard, Devon (GB)

(73) Assignee: MMUNE MACRO-BIOTIC TECHNOLOGY UK LIMITED (GB)

( * ) Notice: Subject to any disclaimer, the term of this patent is extended or adjusted under 35 U.S.C. 154(b) by 0 days.

(21) Appl. No.: 15/527,376

(22) PCT Filed: Nov. 19, 2015

(86) PCT No.: PCT/GB2015/000302
§ 371 (c)(1),
(2) Date: May 17, 2017

(87) PCT Pub. No.: WO2016/079463
PCT Pub. Date: May 26, 2016

(65) Prior Publication Data
US 2017/0319631 A1 Nov. 9, 2017

(30) Foreign Application Priority Data

Nov. 19, 2014 (GB) .................................. 1420515.7
Nov. 5, 2015 (GB) .................................. 1519523.3

(51) Int. Cl.
*A61K 35/63* (2015.01)
*A61K 35/64* (2015.01)

(52) U.S. Cl.
CPC .............. *A61K 35/64* (2013.01); *A61K 35/63* (2015.01)

(58) Field of Classification Search
None
See application file for complete search history.

(56) References Cited

U.S. PATENT DOCUMENTS

2005/0277578 A1  12/2005  Leonard

FOREIGN PATENT DOCUMENTS

| EP | 1 006 124 A1 | 6/2000 |
| GB | 2 368 016 B | 4/2002 |
| WO | 00/74693 A2 | 12/2000 |
| WO | 2009/098490 A1 | 8/2009 |

OTHER PUBLICATIONS

Hui-Yu Yi, et al.; "Insect Antimicrobial Peptides and Their Applications"; Applied Microbiology and Biotechnology, vol. 98, No. 13; Jul. 1, 2014; pp. 5807-5822.
Jaklic Domen, et al; "Selective Antimicrobial Activity of Maggots against Pathogenic Bacteria"; Journal of Medical Microbiology, Society for General Microbiology, vol. 57, No. Pt 5; May 1, 2008; pp. 617-625.
Geetanchaly Nadarasah, et al.; "Insects as Alternative Hosts for Phytopathogenic Bacteria"; FEMS Microbiology Letters, vol. 35, No. 3; May 1, 2011; pp. 555-575.

*Primary Examiner* — Michael Barker
(74) *Attorney, Agent, or Firm* — Ware, Fressola, Maguire & Barber LLP

(57) ABSTRACT

An improved method for the manufacture of a medicament, which method includes the use of tissues, larval forms or derivatives of insects that have been fed on food containing pathogens.

2 Claims, 4 Drawing Sheets

Figure 1. Numbers of Campylobacter in the caecum of birds fed diets supplemented with soya, unstimulated larvae (unstim) or stimulated larvae (stim). Bars indicate significant differences between groups.

Figure 2. Numbers of Lactic acid bacteria in the caecum of birds fed diets supplemented with soya, unstimulated larvae (unstim) or stimulated larvae (stim). No significant differences were seen between groups.

Figure 3. Numbers of enterobacteria in the caecum of birds fed diets supplemented with soya, unstimulated larvae (unstim) or stimulated larvae (stim). No significant differences were seen between groups.

A
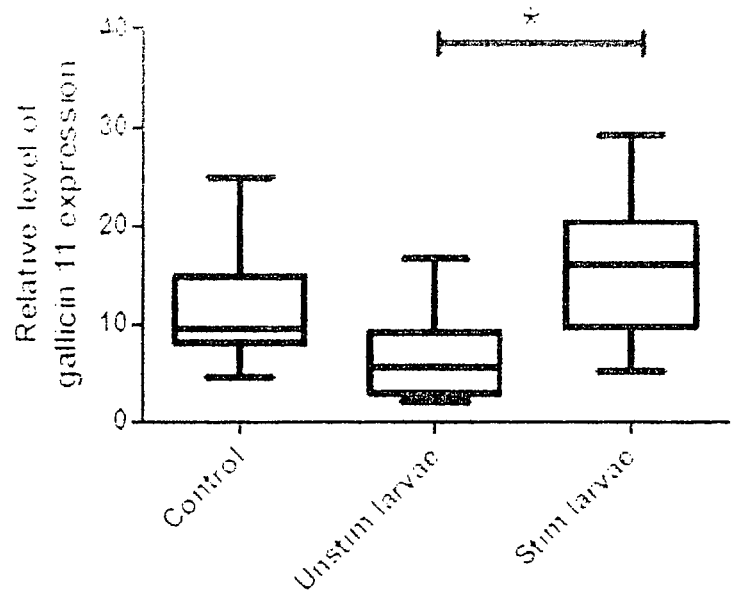
Figure 4
B
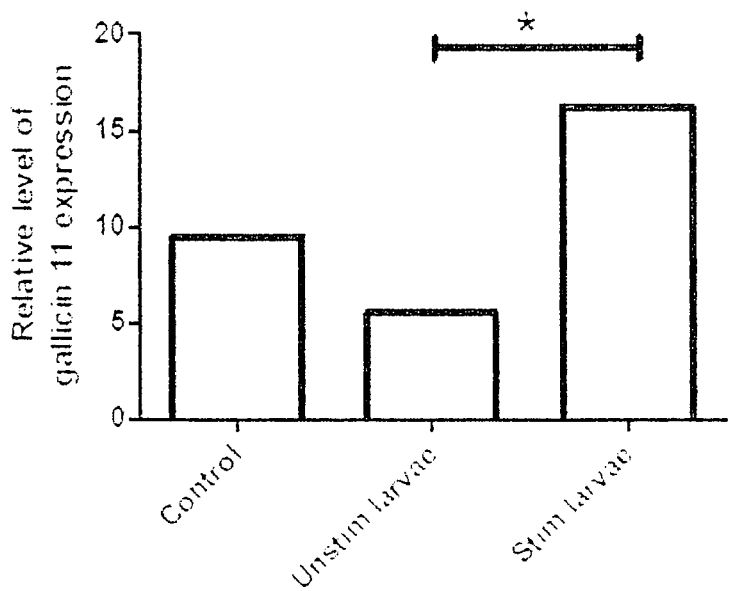

IMMUNITY GENERATION

CROSS REFERENCE TO RELATED APPLICATIONS

This application is the U.S. National Stage of International Application Number PCT/GB2015/000302 filed on Nov. 19, 2015, which application claims priority under 35 USC § 119 to British Patent Application No. 1420515.7 filed on Nov. 19, 2014 and British Patent Application 1519523.3 filed on Nov. 5, 2015. All of these applications are hereby incorporated by reference in their entirety.

FIELD OF THE INVENTION

This invention relates to immunity generation.

BACKGROUND OF THE INVENTION

In British Patent Specification No. 2 368 016 there is described a method for the manufacture of a medicament, which method includes the use of tissues, larval forms or derivatives of insects that have been fed on a food containing pathogens. This method is hereinafter referred to as "a method as defined" and results in the expression of antimicrobial peptides which are hereinafter referred to as AMPs.

It is an object of the present invention to provide improvements in the method as defined.

SUMMARY OF THE INVENTION

According to a first aspect of the present invention there is provided a method as defined in which the expression of AMPs is modulated (maximized) by selectively altering the number or nature of the pathogens that are used.

As applied to the feeding of larvae with bacteria, it has been found that different AMPs are stimulated maximally by different doses of bacteria. Thus, Diptericin expression is favoured by high doses, whereas Sapecin by low doses.

The optimal bacterial/larval combination that has been found to date is *Lucilia serritica* stimulated by *Pseudomonas syringae*, a *bacterium* which is not pathogenic to humans or other animals and is found in the environment.

Thus, according to a second aspect of the present invention, there is provided a method as defined which includes the stimulation of *Lucilia serricata* by *Pseudomonas syringae*.

Exposure of 4-day-old larvae to this *bacterium* for twelve hours has been found to increase AMP expression up to 30-fold as compared to unstimulated larvae. The larvae can be stimulated with live or dead bacteria without affecting larval feed consumption or final weight.

BRIEF DESCRIPTION OF THE DRAWINGS

FIG. 4 shows median levels of Gallicin 11 expression in the caecal tonsil in birds fed either control or unstimulated larval or stimulated larval diets. The asterisk indicates significant differences using Dunn's post hoc test.

DESCRIPTION OF THE PREFERRED EMBODIMENTS

Day-old Ross broiler chicks were housed in biosecure facilities and fed commercial chick crumb supplements with 10% of either soya meal, crushed unstimulated *Lucilia* larvae or crushed unstimulated *Lucilia* larvae.

Insect larvae reared in a milk powder/sucrose/wheat germ/agar mixture for four days were removed from this medium and washed. They were then introduced into fresh growth medium without added bacteria (unstimulated) or containing approximately $5 \times 10^7$ *Pseudomonas syringae* per gram (stimulated). After 24 hours on this medium, the larvae were removed, washed to remove all traces of growth medium and freeze-dried. Once dry, they were crushed using a pestle and mortar to obtain a coarse powder for addition to the chick crumb.

At three days old, birds were infected orally with $10^5$ cfu *Campylobacter jejuni* strain M1.

At eight days old, birds were euthanased and the caeca removed and examined for *Campylobacter*, lactic acid bacteria and *enterobacteria* by serial dilution and spread plating on mCCDA, MRS, and VRBG agars respectively. Differences in the level of bacteria found in the birds were analysed using a Kruskal-Wallis test with Dunn's post test with $P<0.05$ being regarded as significant.

Figure 1:
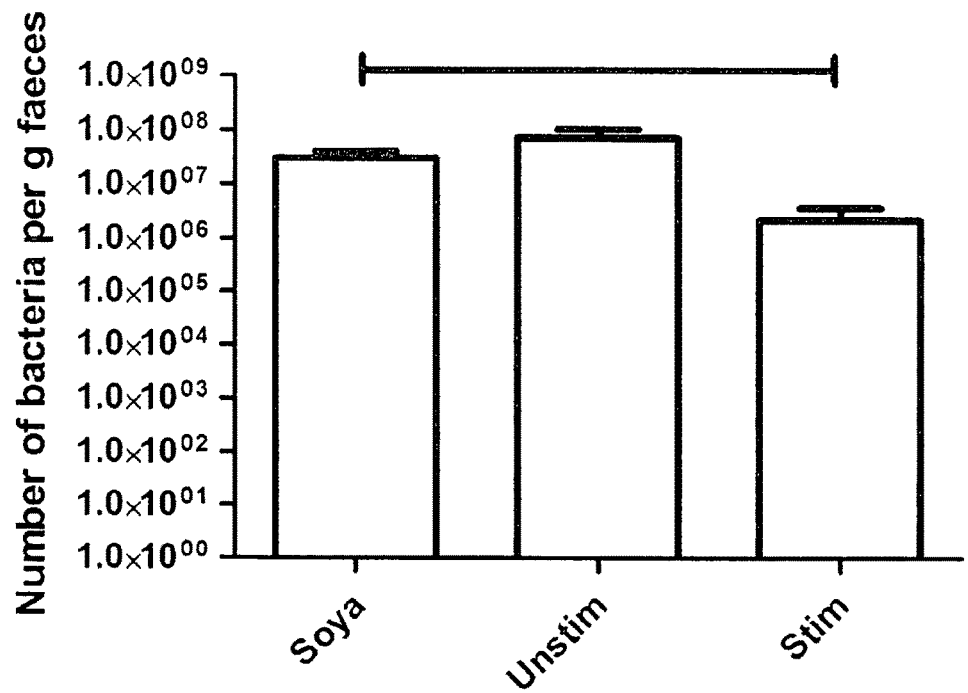
FIG. 1 shows the number of *Camphylobacter* in the caecum of birds fed diets supplemented with soya, unstimulated larvae (unstim) or stimulated larvae (stim). The bars indicate significant differences between groups.
Figure 2:
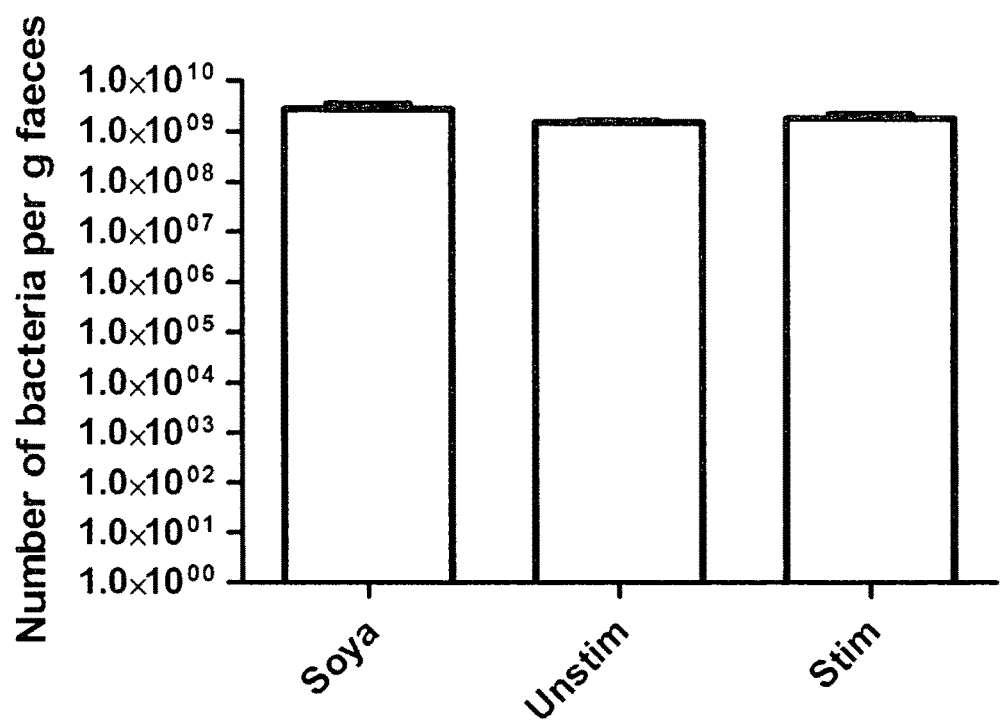
FIG. 2 shows the numbers of lactic acid bacteria in the caecum of birds fed diets supplemented with soya, unstimulated larvae (unstim) or stimulated larvae (stim). No significant differences were seen between groups.
Figure 3:
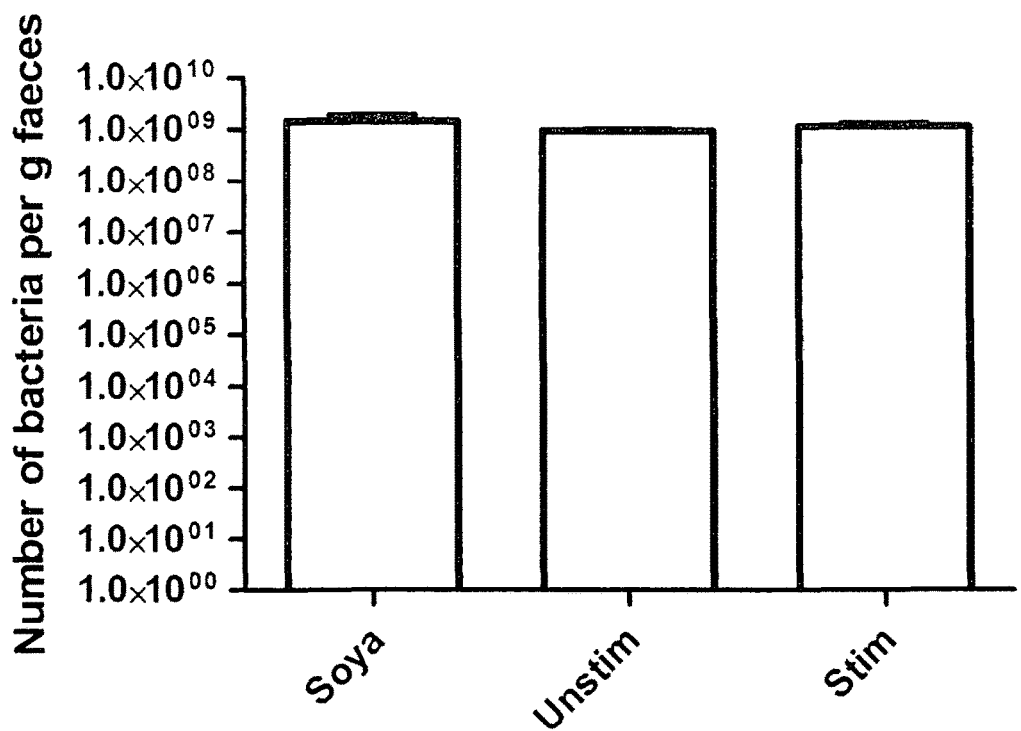
FIG. 3 shows the number of *enterobacteria* in the caecum of birds fed diets supplemented with soya, unstimulated larvae (unstim) or stimulated larvae (stim). No significant differences were seen between groups.

The use of feed containing stimulated larvae resulted in a reduction of *campylobacter* in the caecum (FIG. 1); no effect was seen on numbers of lactic bacteria or *enterobacteria* (FIGS. 2 and 3).

In terms of colonization, 13% of soya fed birds were negative for *campylobacter* in the caecum after eight days, 18% of birds fed unstimulated larvae and 41% of birds fed stimulated larvae. The feed containing stimulated larvae resulted in a significant reduction ($P<0.05$) in the number of birds colonized with *campylobacter* in the caecum as compared to the soya-supplemented control.

Larvae of *Lucilia serricata, Calliphora vacciniae* and *Musca domestica* were assessed for their expression of antimicrobial peptides (AMPs) following stimulation with three different species of bacteria. As bacterial simulation was found to increase AMP expression, experiments have been carried out to investigate the optimal parameters for stimulation of the larvae.

The optimal bacterial/larval combination has been found to be *Lucilia serricata* stimulated by *Pseudomonas* syringe, a *bacterium* which is not pathogenic to animals or humans. Exposure of four-day old larvae to this *bacterium* for twelve hours has been found to increase AMP expression by up to thirty-fold over unstimulated larvae.

Larvae can be stimulated with live or dead bacteria and this does not affect larval feed consumption or final weight. There is also evidence of an interaction between pathogenicity of the *bacterium*, time and dose in affecting AMP expression.

In vitro experiments have been carried out using powder prepared from *Lucilia serricata* larvae stimulated by *Pseudomonas syringae* testing its effectiveness as an antibacterial agent against *Campylobacter jejuni*, with powder from unstimulated larvae used as a control.

Over a three-hour time period, *Campylobacter* bacteria incubated with powder from unstimulated larvae were able to grow whereas the bacterial cultures exposed to 1% w/v powder from larvae stimulated with *Pseudomonas syringae* showed significant bacterial death (P=0.0015).

*Lucilia serricata* larvae challenged with *Pseudomonas syringae* were fed to broiler chicks. The chicks were then infected orally to test their immunity.

Adult *Lucilia serricata* were allowed to lay eggs in a 1:1:1 mixture of wheat germ, yeast and milk powder that had been solidified with agar. This mixture containing eggs was split into portions and at hatch larvae were either challenged with *Pseudomonas syringae* or left unchallenged. After 4 days larvae were harvested, washed to remove feed and freeze dried to a moisture content of 15%. Larvae were then ground to a fine powder in a chilled pestle and mortar.

Groups of 18 day-old Ross broiler chicks were housed in biosecure facilities and fed commercial chick crumb supplemented with 10% w/w of either soya meal (to balance protein levels with feed containing larvae), 10% w/w crushed unstimulated *Lucilia* larvae or 10% w/w crushed stimulated *Lucilia* larvae.

At 3 days old birds were infected orally with $10^5$ cfu *Campylobacter jejuni* strain M1.

At 8 days old birds were euthanased and the caecal tonsil immediately placed into RNAlater. mRNA was extracted using a Qiagen kit and examined for Gallicin 11 expression by quantitative RT-PCR using the primers D11F cagaattgcagaaagccaca and D11R ttctacgtgtgcgtgtgtga with chicken beta actin as a housekeeping gene. Expression of Gallicin 11 was expressed relative to beta actin expression.

Differences between groups of birds were examined for significance using a Kruskal-Wallis test with Dunn's post hoc test as data were not normally distributed.

The results of the test are shown in FIG. 4 of the accompanying drawings. Drawing A is a box and whiskers plot where each box represents the first to third quartile with the median as the line inside the box. The whiskers show the range of data. Drawing B is a histogram showing the median level of expression.

Gallicin 11 was chosen as this has been shown to be expressed in the intestine by others (Hong at et al. Poult. Sci. (2012) 1082).

Diet had a significant effect on Gallicin 11 expression (P=0.0007). In birds fed a diet containing stimulated larvae relative levels of Gallicin 11 expression in the caecum were significantly higher than in birds fed a diet containing unstimulated larvae. This shows that feeding of stimulated larvae, which contain higher amounts of insect AMPs, stimulates host AMP expression. This would give an added stimulation of antibacterial activity in the intestine over and above the provision of fly AMPs in the feed itself.

The invention claimed is:

1. A method for the manufacture of a medicament, comprising the steps of:

exposing larval forms of insects to food containing pathogens for an extended period of time, wherein the larval forms of said insects are at least four days old, and wherein the extended period of time is at least twelve hours;

maximizing an expression of anti-microbial peptides by selectively altering the number or nature of the pathogens:

wherein the larval forms of insects are exposed to *Pseudomonas syringae*; and wherein the larval forms of insects are *Lucilia serricata*.

2. The method for the manufacture of a medicament according to claim 1, wherein the extended period of time is twenty-four hours.

* * * * *